United States Patent [19]
Archibald et al.

[11] Patent Number: 5,821,387
[45] Date of Patent: Oct. 13, 1998

[54] POLYARENES FROM ARYL KETONES WITH APPLICATION TO SYNTHESIS OF CRISNATOL MESYLATE

[75] Inventors: Thomas G. Archibald, Fair Oaks; James C. Barnard, Shingle Springs; Der-Shing Huang, Folsom, all of Calif.

[73] Assignee: Aerojet-General Corporation, Rancho Cordova, Calif.

[21] Appl. No.: 995,501

[22] Filed: Dec. 22, 1997

[51] Int. Cl.$^6$ .................................................. C07C 209/10
[52] U.S. Cl. ......................... 564/405; 564/360; 568/328; 585/642; 585/656
[58] Field of Search .................................. 564/360, 405; 568/328; 585/642, 656

*Primary Examiner*—Brian M. Burn
*Attorney, Agent, or Firm*—Townsend and Townsend and Crew LLP

[57] ABSTRACT

Alkyl-substituted polyarenes of the formula

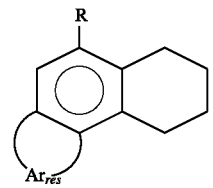

in which R is alkyl and $Ar_{res}$ is an aryl residue, are prepared from aryl ketones by reaction of the latter with 1-cyclohexenyloxytrimethylsilane in the presence of a Friedel-Crafts catalyst. When R is methyl and $Ar_{res}$ is a naphthyl residue, the reaction serves as a step in a reaction scheme leading to crisnatol mesylate, a pharmaceutical useful in the treatment of brain cancer.

16 Claims, No Drawings

POLYARENES FROM ARYL KETONES WITH APPLICATION TO SYNTHESIS OF CRISNATOL MESYLATE

BACKGROUND OF THE INVENTION

1. Field of the Invention

This invention pertains to fused polycyclic aromatic organic compounds (polyarenes), particularly chrysene and compounds of a similar structure, and also to products derived from such compounds, such as crisnatol (2-(6-chrysenylmethylamino)-2-methylpropane-1,3-diol) and crisnatol mesylate (2-(6-chrysenylmethylamino)-2-methylpropane-1, 3-diol methanesulfonate salt).

2. Description of the Prior Art

Polyarenes, or fused polycyclic aromatic compounds, are of interest as intermediates in a variety of useful products. One of these products is a substituted chrysene known as crisnatol mesylate, which is the methanesulfonate salt of 2-(6-chrysenylmethylamino)-2-methylpropane-1,3-diol, and is shown below as Formula I.

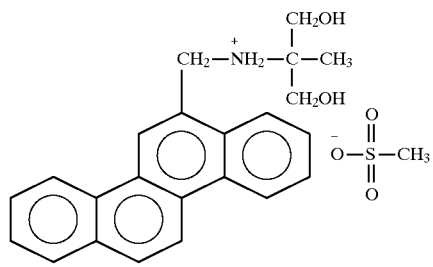

Crisnatol mesylate is a drug that is useful in the treatment of certain forms of brain cancer.

While crisnatol mesylate is naturally occurring as a component of pitch, the natural material is too impure to be suitable for pharmaceutical use. Development of the compound as a useful pharmaceutical therefore requires that the drug be synthesized. Currently known synthesis of the compound uses chrysene (Formula II) as the starting material

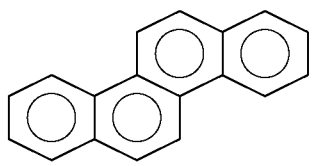

In the synthesis, chrysene is methylated at the no. 6 carbon (i.e., the carbon bearing the substituent in crisnatol mesylate), and the methyl group is further derivatized by subsequent reactions to achieve the final product.

This synthesis suffers from numerous difficulties. One is that chrysene is difficult to prepare and is highly carcinogenic. Another is that the methylation of chrysene produces a mixture of products each bearing methyl groups at different locations, and isolation of 6-methylchrysene from the reaction mixture is difficult and the product is low in yield.

These and other limitations of the prior art are addressed by the present invention.

SUMMARY OF THE INVENTION

The present invention resides in a newly discovered reaction and various reaction schemes that incorporate the new reaction, including a reaction scheme leading to crisnatol and crisnatol mesylate. The newly discovered reaction is the reaction between an aryl ketone having the formula

and 1-cyclohexenyloxytrimethylsilane to form a fused polycyclic aromatic hydrocarbon having the formula

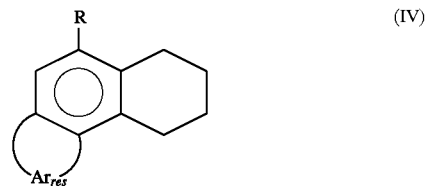

In these formulas, the symbol "Ar" represents an aryl group, the symbol "$Ar_{res}$" represents the residue of Ar minus two adjacent aromatic ring carbon atoms, and the symbol "R" represents a $C_1$-$C_8$ alkyl group. This reaction avoids the formation and handling of chrysene, and achieves the precise placement of the alkyl group at the location needed for crisnatol synthesis (i.e., at the 6-position on chrysene when Ar is a naphthyl group and the reaction is followed by a dehydrogenation of the cyclohexenyl ring at the right end of the formula), and does so in high yield.

Thus, when the aryl ketone is 1-naphthylacetone, the reaction can be used to form 6-methyl-7,8,9,10-tetrahydrochrysene, which can then be dehydrogenated to form 6-methylchrysene. The latter can be brominated at the methyl group, and the brominated product reacted with 2-amino-2-methylpropane-1,3-diol to form crisnatol, which can then be reacted with methanesulfonic acid to form crisnatol mesylate.

These and other features, aspects and advantages of the invention will become apparent from the description that follows.

DETAILED DESCRIPTION OF THE INVENTION AND PREFERRED EMBODIMENTS

In the aryl ketone (Formula III) serving as the starting material in the reaction to produce the alkyl-substituted tetrahydropolyarene represented by Formula IV, the "Ar" group is either a monocyclic or polycyclic aryl group, such as phenyl naphthyl, or anthracyl. Phenyl and naphthyl groups are preferred, with naphthyl being of particular interest when the reaction is used to form a polyarene precursor to crisnatol. The aryl residue "$Ar_{res}$" in Formula IV is the same aryl group as Formula III fused to the phenyl ring shown in Formula IV at the two vertices at the lower left of the ring. The symbol "$Ar_{res}$" taken together with these two vertices thus completes the "Ar" group of Formula III.

The "R" group common to both Formulas III and IV is an alkyl group, either straight-chain or branched, saturated and preferably from 1 to 8 carbon atoms in length. Preferred R groups are $C_1$-$C_4$ linear alkyl groups. The methyl group is of particular interest when the reaction is used to form a polyarene precursor to crisnatol.

Aryl ketones are either commercially available or readily synthesized by known techniques. One method of synthesis is the reaction of an aryl carboxylic acid with an appropriate acid anhydride. 1-Naphthylacetone, for example, can thus be prepared by reacting 1-naphthylacetic acid with acetic anhydride. Alternatively, the aryl aldehyde can be reacted with a nitroalkane in which the alkane is a primary alkane, "primary" being defined as above, followed by a reduction of the aryl nitroolefin to the aryl ketone. For the 1-naphthylacetone example, therefore, 1-naphthylaldehyde can be reacted with nitroethane followed by reduction with iron powder to form 1-naphthylacetone.

The reaction is performed in the presence of a Friedel-Crafts catalyst, preferably a Lewis acid-type catalyst. Examples of catalysts meeting this description are well known in the art, and include $AlCl_3$, $AlBr_3$, $BeCl_2$, $CdCl_2$, $ZnCl_2$, $BF_3$, $BCl_3$, $BBr_3$, $GaCl_3$, $GaBr_3$, $TiCl_4$, $ZrCl_4$, $SnCl_4$, $SnBr_4$, $SbCl_5$, $BiCl_3$, $FeCl_3$, and $UCl_4$. A particularly preferred catalyst is $TiCl_4$. The catalyst is included in the reaction mixture in a catalytic amount, which term is used herein to denote any amount that will accelerate the rate of reaction, preferably to a degree that will provide an economically favorable reaction, i.e., a high yield within an economically justifiable period of time. This may vary with the specific starting materials (i.e., the particular "Ar" and "R" in the aryl ketone formula), the specific catalyst selected, the operating conditions, and the economics of the particular operation where the reaction is performed. Using $TiCl_4$, for example, best results in most cases will be obtained with an excess of moles of catalyst to aryl ketone, for example a catalyst:ketone mole ratio of from about 1.5:1 to about 10:1, and preferably about 2:1 to about 5:1.

The amount of 1-cyclohexenyloxytrimethylsilane relative to the aryl ketone can also vary. It is preferred that a molar excess of 1-cyclohexenyloxytrimethylsilane be used. Best results can generally be obtained with an aryl ketone: 1-cyclohexenyloxytrimethylsilane mole ratio of from about 0.10:1 to about 0.75:1, and preferably from about 0.25:1 to about 0.50:1.

The reaction is preferably performed in an inert organic solvent, the selection being readily apparent to the routinely skilled synthesis chemist, and also in an inert atmosphere. The reaction temperature can vary, although care should be taken to avoid polymerization of the 1-cyclohexenyloxytrimethylsilane, which occurs readily at temperatures above about 10° C. A preferred temperature range is from about −20° C. to about +10° C., and a more preferred temperature range is from about −10° C. to about +5° C. The product is then recovered by conventional recovery and purification methods.

The product of this reaction contains one saturated ring fused with the remaining rings, as shown in Formula IV. In the crisnatol synthesis, the reaction described above is followed by a dehydrogenation reaction to convert this ring to an aromatic ring. A conventional dehydrogenation catalyst can be used, common examples of which are platinum and palladium. The reaction can be performed in a conventional solvent such as triglyme, and preferably at elevated temperature. Details of the reaction conditions and procedures will be readily apparent to those skilled in the art.

In the crisnatol synthesis, the product of the dehydrogenation reaction is 2-methylchrysene, which is subsequently brominated to form 6-bromomethylchrysene. Conventional brominating agents and conditions can be employed. Examples of brominating agents are N-bromosuccinimide, tribromoacetic acid, bromine chloride, ferric bromide, and 2,4,4,6-tetrabromo-2,5-cyclohexadiene-1-one.

Once formed, the 6-bromomethylchrysene can be converted to 2-(6-chrysenylmethylamino)-2-methylpropane-1,3-diol (crisnatol) by reaction with 2-amino-2-methylpropane-1,3-diol. The crisnatol can then be converted to the methylsulfonate salt (crisnatol mesylate) by reaction with methanesulfonic acid. Both of these are known reactions, and the proportions, additional reagents or system components and operating conditions will be readily apparent to the routinely skilled synthesis chemist.

The following examples are offered for purposes of illustration, and are not intended to impose limits on the invention.

EXAMPLES

In the following procedures, NMR analyses were performed on a Bruker MSL-300 spectrometer at 300 MHz in deuterochloroform or deuterated dimethyl sulfoxide solution with proton and carbon shifts in ppm relative to tetramethylsilane; IR analyses were by diffuse reflectance and were performed on a Nicolet SX-5 spectrometer on potassium bromide; and thermal analyses were performed on a DuPont DSC 9100 Analyzer.

Preparation of 1-Naphthyl-2-nitropropene

A solution of 1-naphthylaldehyde (624.8 g, 4.0 mol), nitroethane (300.0 g, 4 mol) and n-butylamine (14.8 g, 0.20 mol) was refluxed in ethanol (400 mL) for 24 hours. The mixture was cooled, diluted with methanol (200 mL), and filtered to give 767 g (90% yield) of 1-naphthyl-2-nitropropene. Upon standing, an additional 60 g (97% total yield) of 1-naphthyl-2-nitropropene crystallized from solution.

Preparation of 1-Naphthylacetone

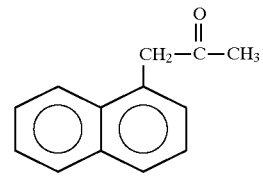

A mixture of 1-naphthyl-2-nitropropene (taken directly from the synthesis of the last paragraph without purification, 10.4 g, 0.8 mol), iron powder (320.0 g, 5.8 g-atoms), ferric chloride hexahydrate (0.8 g) and water (800 mL) was mechanically stirred and heated to 85° C. Hydrochloric acid (37% aqueous, 120 mL, 1.2 mol) was then added dropwise over 5 hours while the temperature was maintained at 85–90° C. The mixture was filtered, the filtrate was extracted with methylene chloride (100 mL), and the residual solids were extracted with methylene chloride (2×200 mL). The combined organic extracts were washed with water, dried over $MgSO_4$ and evaporated to give 139.6 g of 1-naphthylacetone that was shown by gas-liquid chromatography to be approximately 95% pure (91% yield). Further purification was achieved by recrystallization from methanol at −78° C. $^1H$ NMR 2.10 (s, 3 H), 4.11 (s, 2 H), 7.4 (m, 4 H), 7.8 (m, 3 H).

Preparation of 6-Methyl-7,8,9,10-tetrahydrochrysene

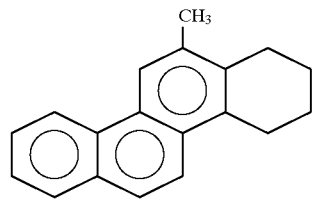

A solution of 1-naphthylacetone (27.6 g, 0.15 mol) in methylene chloride (450 mL) was stirred under nitrogen and 1-cyclohexenyloxytrimethylsilane (51.1 g, 0.30 mol) was added. The solution was cooled to 5° C. with an ice bath.

Titanium tetrachloride (85.4 g, 0.45 mol) was added over 50 minutes, the rate of addition being sufficiently slow to maintain the reaction temperature at or below 10° C. The resulting solution was stirred for one hour. Water was then added (300 mL) and the mixture was permitted to warm to ambient temperature. The organic layer was separated, washed with water (300 mL) and sodium carbonate solution (1 M, 300 mL), and dried over $MgSO_4$. The solvent was removed in vacuo, and the solid residue was refluxed for one hour with isopropyl alcohol (300 mL), cooled and filtered. The solids were washed with isopropyl alcohol (50 mL) and dried to give 25.82 g (70% yield) of 6-methyl-7,8,9,10-tetrahydrochrysene. $^1$H NMR 1.95 (m, 4 H), 2.44 (s, 3 H), 2.77 (t, J=7 Hz, 2 H), 3.16 (t, J=7 Hz, 2 H), 7.54 (m, 4 H), 7.66 (d, J=9.1 Hz, 1 H), 7.83 (d, J=7.7 Hz), 7.90 (d, J=9.1 Hz, 1H), 8.32 (s, 1 H), 8.64 (d, J=8.2 Hz, 1 H).

Preparation of 6-Methylchrysene

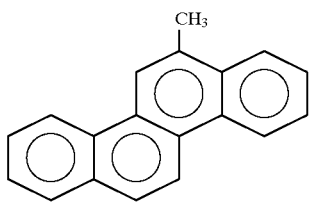

A mixture of palladium on carbon (10%, 5.0 g) and 6-methyl-7,8,9,10-tetrahydro-chrysene (64.0 g, 0.24 mol) in triglyme (290 mL) was heated at 210° C. under a slow nitrogen stream. The progress of the reaction was monitored by NMR analysis that showed the reaction was 72% complete after 4 hours. The heating was discontinued after 18 hours when essentially all of the starting material had been consumed. The mixture was cooled to 100° C. and filtered to remove the catalyst. The solution was then cooled further to 0° C., and filtered to give 42.9 g (68% yield) of 6-methylchrysene. The filtrate was diluted with water (300 mL) and filtered to give an additional 15.5 g (93% combined yield) of 6-methylchrysene. $^1$H NMR (CDCl$_3$) 2.86 (s, 3 H), 7.6 (m, 4 H), 7.9 (m, 2 H), 8.1 (m, 1 H), 8.55 (s, 1 H), 8.65 (m, 1 H), 8.8 (m, 2 H).

Preparation of 6-Bromomethylchrysene

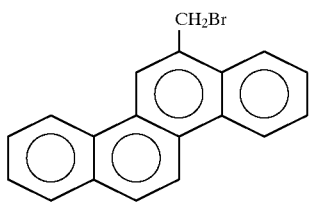

A solution of 6-methylchrysene (4,85 g, 20 mmol), N-bromosuccinimide (3.60 g, 20.2 mmol), and benzoyl peroxide (0.242 g, 1.0 mmol) in chlorobenzene (100 mL) was heated under nitrogen at 80° C. After 1 hour, NMR analysis indicated that the starting material had been consumed. The solution was cooled to 50° C. at which point a solid precipitate had formed. The mixture was diluted with methanol (100 mL) and further cooled to ambient temperature. The mixture was filtered and the solid washed with methanol to give 4.87 g (76% yield) of 6-bromomethylchrysene. $^1$H NMR (CDCl$_3$) 5.17 (s, 2H), 7.25 (m, 4 H), 8.0 (t, J=8.7 Hz, 2 H), 8.31 (m, 1 H), 8.67 (d, J=9.0 Hz), 8.75 (d, J=9.0 Hz, 1 H), 8.81 (m, 2 H).

Preparation of 2-(6-Chrysenylmethylamino)-2-methylpropane-1,3-diol (Crisnatol)

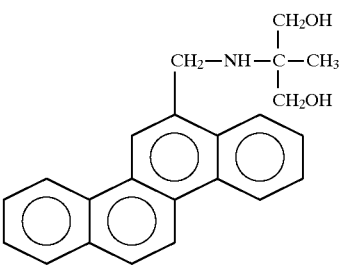

A mixture of 6-bromomethylchrysene (4.82 g, 15 mmol), 2-amino-2-methylpropane-1,3diol (3.15 g, 30 mmol), and triethylamine (1.67 g, 16.5 mmol) was refluxed in tetrahydrofuran (75 mL) under nitrogen. After one hour all the solids had dissolved and NMR analysis indicated that the 6-bromomethylchrysene had been consumed. Water (150 mL) was added and the mixture was cooled to ambient temperature. The solids were collected by filtration, washed with water (3×30 mL), and dried in vacuo to give 3.67 g (71% yield) of 2-(6-chrysenylmethylamino)-2-methylpropane-1,3diol. $^1$H NMR (CDCl$_3$) 1.19 (s, 3 H), 1.81 (br s, 1 H), 3.53 (d, J=5.0 Hz, 2 H), 4.39 (s, 2 H), 4.58 (t, J=5.0 Hz, 2 H), 7.78 (m, 4 H), 8.11 (m, 2 H), 8.45 (d, J=8.4 Hz, 1 H), 8.9 (m, 4 H).

Preparation of 2-(6-Chrysenylmethylamino)-2-methylpropane-1,3-diol Methanesulfonate Salt (Crisnatol Mesylate)

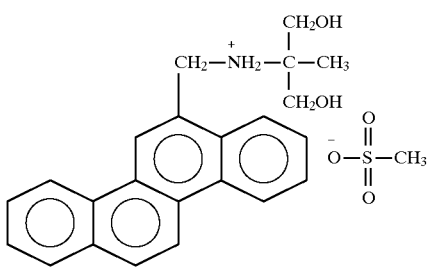

A solution of 2-(6-chrysenylmethylamino)-2-methylpropane-1,3-diol (3.45 g, 10 mmol) in tetrahydrofuran (75 mL) was heated to reflux under nitrogen. Methanesulfonic acid (1.06 g, 11 mmol) was then added and a precipitate formed. The mixture was cooled to ambient temperature, stirred for 30 minutes, and filtered. The solid was washed with tetrahydrofuran (2×10 mL) and dried in vacuo to give 4.08 g (93% yield) of the desired methylsulfonate salt. Recrystallization of the salt from ethanol gave purified material. $^1$H NMR (DMSO-d6) 1.42 (s, 3 H), 2.33 (s, 3 H), 3.79 (s, 4 H), 4.88 (br s, 2 H), 5.65 (s, 2 H), 7.77 (m, 4 H), 8.16 (t, 2H), 8.42 (d, 1H), 8.70 (s, 2 H), 8.90 (m, 4 H); $^{13}$C NMR 16.376, 42.562, 61.472, 63.984, 121.159, 123.378, 123.971, 123.318, 125.179, 126.697, 126.843, 127.015, 127.441, 128.258, 128.310, 128.492, 130.039, 130.309, 131.833.

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention.

We claim:

1. A method for preparing a fused polycyclic aromatic hydrocarbon of the formula

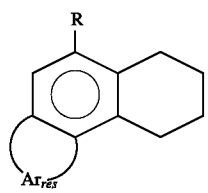

in which:
- $Ar_{res}$ is the residue of an aryl compound minus two adjacent aromatic ring carbon atoms, and
- R is a $C_1$–$C_8$ alkyl group, said method comprising reacting an aryl ketone of the structure

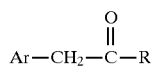

in which Ar is the aryl compound of which $Ar_{res}$ is the residue, with 1-cyclohexenyloxy- trimethylsilane in the presence of a catalytic amount of a Friedel-Crafts catalyst.

2. A method in accordance with claim 1 in which R is a $C_1$–$C_4$ linear alkyl group.

3. A method in accordance with claim 1 in which R is methyl.

4. A method in accordance with claim 1 in which Ar is a member selected from the group consisting of phenyl and naphthyl, and $Ar_{res}$ is correspondingly a phenyl residue or a naphthyl residue minus two adjacent ring carbon atoms.

5. A method in accordance with claim 1 in which said Friedel-Crafts catalyst is $TiCl_4$.

6. A method in accordance with claim 1 in which R is methyl, Ar is naphthyl, $Ar_{res}$ is a naphthyl residue minus two adjacent ring carbon atoms, and said Friedel-Crafts catalyst is $TiCl_4$.

7. A method in accordance with claim 1, said method comprising reacting said aryl ketone with said 1-cyclohexenyloxytrimethylsilane in the presence of said catalyst at a temperature of from about −20° C. to about +10° C.

8. A method in accordance with claim 1, said method comprising reacting said aryl ketone with said 1-cyclohexenyloxytrimethylsilane in the presence of said catalyst at a temperature of from about −10° C. to about +5° C.

9. A method in accordance with claim 1, said method comprising contacting said 1-cyclohexenyloxytrimethylsilane with said aryl ketone at an aryl ketone: 1-cyclo- hexenyloxytrimethylsilane mole ratio of from about 0.10:1 to about 0.75:1.

10. A method in accordance with claim 1, said method comprising contacting said 1-cyclohexenyloxytrimethylsilane with said aryl ketone at an aryl ketone: 1-cyclo- hexenyloxytrimethylsilane mole ratio of from about 0.25:1 to about 0.5:1.

11. A method for preparing 2-(6-chrysenylmethylamino)-2-methylpropane- 1,3-diol, said method comprising:
(a) reacting 1-naphthylacetone with an excess of 1-cyclohexenyloxytrimethylsilane in the presence of a catalytic amount of a Friedel-Crafts catalyst to form 6-methyl-7,8,9, 10-tetrahydrochrysene;
(b) dehydrogenating said 6-methyl-7,8,9,10-tetrahydrochrysene thus formed over a dehydrogenation catalyst to form 6-methylchrysene;
(c) brominating said 6-methylchrysene thus formed with an brominating agent to form 6-bromomethylchrysene; and
(d) reacting said 6-bromomethylchrysene thus formed with 2-amino-2-methylpropane- 1,3-diol to form 2-(6-chrysenylmethylamino)-2-methylpropane-1,3-diol.

12. A method in accordance with claim 11 in which said Friedel-Crafts catalyst of (a) is $TiCl_4$.

13. A method in accordance with claim 11 in which (a) is performed at a temperature of from about −20° C. to about +10° C.

14. A method in accordance with claim 11 in which (a) is performed at a temperature of from about −10° C. to about +50° C.

15. A method in accordance with claim 11 in which (a) is performed with a 1-naphthylacetone: 1-cyclohexenyloxytrimethylsilane mole ratio of from about 0.10:1 to about 0.75:1.

16. A method in accordance with claim 11 in which (a) is performed with a 1-naphthylacetone: 1-cyclohexenyloxytrimethylsilane mole ratio of from about 0.25:1 to about 0.5:1.

* * * * *